(12) United States Patent
Butcher

(10) Patent No.: US 8,679,140 B2
(45) Date of Patent: Mar. 25, 2014

(54) SURGICAL CLAMPING DEVICE WITH RATCHETING GRIP LOCK

(75) Inventor: Dennis W. Butcher, Longmont, CO (US)

(73) Assignee: Covidien LP, Mansfield, MA (US)

(*) Notice: Subject to any disclaimer, the term of this patent is extended or adjusted under 35 U.S.C. 154(b) by 0 days.

(21) Appl. No.: 13/483,733

(22) Filed: May 30, 2012

(65) Prior Publication Data

US 2013/0325043 A1 Dec. 5, 2013

(51) Int. Cl.
*A61B 17/08* (2006.01)

(52) U.S. Cl.
USPC .......................... 606/157; 606/208

(58) Field of Classification Search
USPC ........... 30/262, 271; 81/313, 314; 606/51, 52, 606/151, 157, 158, 174, 205, 206, 207, 208
See application file for complete search history.

(56) References Cited

U.S. PATENT DOCUMENTS

| | | | |
|---|---|---|---|
| 107,577 A * | 9/1870 | Will | 30/250 |
| 3,459,187 A | 8/1969 | Pallotta | |
| 3,866,610 A | 2/1975 | Kletschka | |
| 3,911,766 A | 10/1975 | Fridolph et al. | |
| 3,952,749 A | 4/1976 | Fridolph et al. | |
| D249,549 S | 9/1978 | Pike | |
| D263,020 S | 2/1982 | Rau, III | |
| 4,448,194 A * | 5/1984 | DiGiovanni et al. | 606/145 |
| 4,662,372 A | 5/1987 | Sharkany et al. | |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| 5,209,747 A | 5/1993 | Knoepfler | |
| 5,211,655 A | 5/1993 | Hasson | |
| 5,219,354 A | 6/1993 | Choudhury et al. | |
| 5,250,056 A | 10/1993 | Hasson | |
| 5,269,804 A | 12/1993 | Bales et al. | |
| D343,453 S | 1/1994 | Noda | |
| 5,304,203 A | 4/1994 | El-Mallawany et al. | |
| 5,308,357 A | 5/1994 | Lichtman | |
| 5,318,589 A | 6/1994 | Lichtman | |
| D348,930 S | 7/1994 | Olson | |
| D349,341 S | 8/1994 | Lichtman et al. | |
| 5,350,391 A | 9/1994 | Iacovelli | |

(Continued)

FOREIGN PATENT DOCUMENTS

| | | |
|---|---|---|
| CA | 2104423 | 2/1994 |
| CA | 2590520 | 11/2007 |

(Continued)

OTHER PUBLICATIONS

U.S. Appl. No. 08/926,869, filed Sep. 10, 1997, James G. Chandler.

(Continued)

*Primary Examiner* — Ryan Severson
*Assistant Examiner* — Jonathan W Miles

(57) ABSTRACT

At least on aspect of the present disclosure relates to a surgical clamping device, comprising first and second shaft members each having a jaw member disposed at a distal end thereof, a gripping member disposed on the first shaft member, and a gear system disposed on the second shaft member and configured to receive the gripping member and incrementally lock the gripping member in at least one predefined position.

18 Claims, 3 Drawing Sheets

(56) References Cited

U.S. PATENT DOCUMENTS

| | | |
|---|---|---|
| D354,564 S | 1/1995 | Medema |
| 5,389,098 A | 2/1995 | Tsuruta et al. |
| 5,403,342 A | 4/1995 | Tovey et al. |
| D358,887 S | 5/1995 | Feinberg |
| 5,476,479 A | 12/1995 | Green et al. |
| 5,480,409 A | 1/1996 | Riza |
| 5,520,702 A | 5/1996 | Sauer et al. |
| 5,536,251 A | 7/1996 | Evard et al. |
| 5,582,611 A | 12/1996 | Tsuruta et al. |
| 5,601,601 A | 2/1997 | Tai et al. |
| 5,603,723 A | 2/1997 | Aranyi et al. |
| 5,607,436 A | 3/1997 | Pratt et al. |
| 5,611,813 A | 3/1997 | Lichtman |
| 5,618,307 A * | 4/1997 | Donlon et al. ............... 606/205 |
| 5,620,459 A | 4/1997 | Lichtman |
| 5,626,607 A | 5/1997 | Malecki et al. |
| 5,626,609 A | 5/1997 | Zvenyatsky et al. |
| 5,643,294 A | 7/1997 | Tovey et al. |
| D384,413 S | 9/1997 | Zlock et al. |
| 5,700,270 A | 12/1997 | Peyser et al. |
| H1745 H | 8/1998 | Paraschac |
| 5,792,165 A | 8/1998 | Klieman et al. |
| 5,797,927 A | 8/1998 | Yoon |
| 5,797,958 A | 8/1998 | Yoon |
| 5,810,877 A | 9/1998 | Roth et al. |
| 5,827,323 A | 10/1998 | Klieman et al. |
| 5,833,695 A | 11/1998 | Yoon |
| D402,028 S | 12/1998 | Grimm et al. |
| D408,018 S | 4/1999 | McNaughton |
| 5,893,863 A | 4/1999 | Yoon |
| 5,935,126 A | 8/1999 | Riza |
| 5,954,731 A | 9/1999 | Yoon |
| 5,957,937 A | 9/1999 | Yoon |
| D416,089 S | 11/1999 | Barton et al. |
| 5,984,932 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 6,017,358 A | 1/2000 | Yoon et al. |
| D424,694 S | 5/2000 | Tetzlaff et al. |
| D425,201 S | 5/2000 | Tetzlaff et al. |
| 6,099,537 A | 8/2000 | Sugai et al. |
| 6,099,550 A | 8/2000 | Yoon |
| 6,117,158 A | 9/2000 | Measamer et al. |
| H1904 H | 10/2000 | Yates et al. |
| 6,139,563 A | 10/2000 | Cosgrove, III et al. |
| 6,174,309 B1 | 1/2001 | Wrublewski et al. |
| 6,214,028 B1 | 4/2001 | Yoon et al. |
| 6,270,508 B1 | 8/2001 | Klieman et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| 6,461,368 B2 | 10/2002 | Fogarty et al. |
| D465,281 S | 11/2002 | Lang |
| D466,209 S | 11/2002 | Bon |
| 6,556,100 B2 | 4/2003 | Takamine |
| 6,638,287 B2 | 10/2003 | Danitz et al. |
| 6,641,595 B1 | 11/2003 | Moran et al. |
| 6,676,676 B2 | 1/2004 | Danitz et al. |
| 6,743,239 B1 | 6/2004 | Kuehn et al. |
| D493,888 S | 8/2004 | Reschke |
| D496,997 S | 10/2004 | Dycus et al. |
| D499,181 S | 11/2004 | Dycus et al. |
| 6,824,547 B2 | 11/2004 | Wilson, Jr. et al. |
| D502,994 S | 3/2005 | Blake, III |
| 6,935,031 B1 * | 8/2005 | Huang ............... 30/250 |
| D509,297 S | 9/2005 | Wells |
| 6,976,992 B2 | 12/2005 | Sachatello et al. |
| 6,977,495 B2 | 12/2005 | Donofrio |
| 6,981,628 B2 | 1/2006 | Wales |
| 7,041,102 B2 | 5/2006 | Truckai et al. |
| D525,361 S | 7/2006 | Hushka |
| 7,083,618 B2 | 8/2006 | Couture et al. |
| 7,090,673 B2 | 8/2006 | Dycus et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| D531,311 S | 10/2006 | Guerra et al. |
| 7,118,570 B2 * | 10/2006 | Tetzlaff et al. ............... 606/48 |
| 7,118,587 B2 | 10/2006 | Dycus et al. |
| 7,131,970 B2 | 11/2006 | Moses et al. |
| 7,131,971 B2 | 11/2006 | Dycus et al. |
| D533,274 S | 12/2006 | Visconti et al. |
| D533,942 S | 12/2006 | Kerr et al. |
| 7,147,638 B2 | 12/2006 | Chapman et al. |
| D535,027 S | 1/2007 | James et al. |
| 7,160,299 B2 | 1/2007 | Baily |
| D538,932 S | 3/2007 | Malik |
| D541,418 S | 4/2007 | Schechter et al. |
| 7,204,835 B2 | 4/2007 | Latterell et al. |
| 7,208,005 B2 | 4/2007 | Frecker et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee |
| 7,246,734 B2 | 7/2007 | Shelton, IV |
| 7,252,667 B2 | 8/2007 | Moses et al. |
| 7,255,697 B2 | 8/2007 | Dycus et al. |
| 7,267,677 B2 | 9/2007 | Johnson et al. |
| 7,329,256 B2 | 2/2008 | Johnson et al. |
| D564,662 S | 3/2008 | Moses et al. |
| D567,943 S | 4/2008 | Moses et al. |
| 7,384,420 B2 | 6/2008 | Dycus et al. |
| D575,395 S | 8/2008 | Hushka |
| D575,401 S | 8/2008 | Hixson et al. |
| D582,038 S | 12/2008 | Swoyer et al. |
| 7,473,253 B2 | 1/2009 | Dycus et al. |
| 7,491,201 B2 | 2/2009 | Shields et al. |
| 7,500,975 B2 | 3/2009 | Cunningham et al. |
| 7,510,556 B2 | 3/2009 | Nguyen et al. |
| 7,513,898 B2 | 4/2009 | Johnson et al. |
| 7,553,312 B2 | 6/2009 | Tetzlaff et al. |
| 7,582,087 B2 | 9/2009 | Tetzlaff et al. |
| 7,597,693 B2 | 10/2009 | Garrison |
| 7,628,791 B2 | 12/2009 | Garrison et al. |
| 7,686,827 B2 | 3/2010 | Hushka |
| 7,708,735 B2 | 5/2010 | Chapman et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,753,909 B2 | 7/2010 | Chapman et al. |
| D621,503 S | 8/2010 | Otten et al. |
| 7,766,910 B2 | 8/2010 | Hixson et al. |
| 7,771,425 B2 | 8/2010 | Dycus et al. |
| 7,780,662 B2 | 8/2010 | Bahney |
| 7,811,283 B2 | 10/2010 | Moses et al. |
| D627,462 S | 11/2010 | Kingsley |
| D628,289 S | 11/2010 | Romero |
| D628,290 S | 11/2010 | Romero |
| 7,828,792 B2 | 11/2010 | McNally et al. |
| 7,846,161 B2 | 12/2010 | Dumbauld et al. |
| 7,855,007 B2 | 12/2010 | Gross et al. |
| 7,857,812 B2 | 12/2010 | Dycus et al. |
| D630,324 S | 1/2011 | Reschke |
| 7,877,852 B2 | 2/2011 | Unger et al. |
| 7,877,853 B2 | 2/2011 | Unger et al. |
| 7,879,035 B2 | 2/2011 | Garrison et al. |
| 7,887,536 B2 | 2/2011 | Johnson et al. |
| 7,896,878 B2 | 3/2011 | Johnson et al. |
| 7,909,823 B2 | 3/2011 | Moses et al. |
| 7,922,718 B2 | 4/2011 | Moses et al. |
| D649,249 S | 11/2011 | Guerra |
| D649,643 S | 11/2011 | Allen, IV et al. |
| 8,070,746 B2 | 12/2011 | Orton et al. |
| 8,070,748 B2 | 12/2011 | Hixson et al. |
| 8,080,004 B2 * | 12/2011 | Downey et al. ............... 606/1 |
| 8,128,624 B2 | 3/2012 | Couture et al. |
| 8,136,252 B2 * | 3/2012 | Linden et al. ............... 30/192 |

(56) References Cited

U.S. PATENT DOCUMENTS

| | | | |
|---|---|---|---|
| 8,147,489 B2* | 4/2012 | Moses et al. | 606/51 |
| 8,166,659 B2* | 5/2012 | Huang | 30/254 |
| D661,394 S | 6/2012 | Romero et al. | |
| 8,197,479 B2 | 6/2012 | Olson et al. | |
| 8,225,513 B2* | 7/2012 | Huang | 30/254 |
| 8,241,282 B2 | 8/2012 | Unger et al. | |
| 8,241,284 B2 | 8/2012 | Dycus et al. | |
| 8,303,586 B2* | 11/2012 | Cunningham et al. | 606/51 |
| 8,327,549 B2* | 12/2012 | Huang | 30/251 |
| 8,357,159 B2* | 1/2013 | Romero | 606/51 |
| 8,361,071 B2* | 1/2013 | Tetzlaff et al. | 606/51 |
| 2002/0188294 A1 | 12/2002 | Couture et al. | |
| 2003/0014053 A1 | 1/2003 | Nguyen et al. | |
| 2003/0018831 A1 | 1/2003 | Lebena | |
| 2003/0109875 A1 | 6/2003 | Tetzlaff et al. | |
| 2003/0181910 A1 | 9/2003 | Dycus et al. | |
| 2003/0220637 A1 | 11/2003 | Truckai et al. | |
| 2003/0229344 A1 | 12/2003 | Dycus et al. | |
| 2004/0082952 A1 | 4/2004 | Dycus et al. | |
| 2004/0116924 A1 | 6/2004 | Dycus et al. | |
| 2004/0162557 A1 | 8/2004 | Tetzlaff et al. | |
| 2004/0243125 A1 | 12/2004 | Dycus et al. | |
| 2004/0249374 A1 | 12/2004 | Tetzlaff et al. | |
| 2005/0149017 A1 | 7/2005 | Dycus | |
| 2005/0197659 A1 | 9/2005 | Bahney | |
| 2006/0052778 A1 | 3/2006 | Chapman et al. | |
| 2006/0084973 A1 | 4/2006 | Hushka | |
| 2006/0089670 A1 | 4/2006 | Hushka | |
| 2006/0189981 A1 | 8/2006 | Dycus et al. | |
| 2007/0043352 A1 | 2/2007 | Garrison et al. | |
| 2007/0043353 A1 | 2/2007 | Dycus et al. | |
| 2007/0062017 A1 | 3/2007 | Dycus et al. | |
| 2007/0078458 A1 | 4/2007 | Dumbauld et al. | |
| 2007/0088356 A1 | 4/2007 | Moses et al. | |
| 2007/0106295 A1 | 5/2007 | Garrison et al. | |
| 2007/0142833 A1 | 6/2007 | Dycus et al. | |
| 2007/0156140 A1 | 7/2007 | Baily | |
| 2007/0179499 A1 | 8/2007 | Garrison | |
| 2007/0260242 A1 | 11/2007 | Dycus et al. | |
| 2008/0033428 A1 | 2/2008 | Artale et al. | |
| 2008/0074417 A1 | 3/2008 | Mejdrich et al. | |
| 2008/0079890 A1 | 4/2008 | Sugahara | |
| 2008/0082100 A1 | 4/2008 | Orton et al. | |
| 2008/0114356 A1 | 5/2008 | Johnson et al. | |
| 2008/0167452 A1 | 7/2008 | Maiti et al. | |
| 2008/0167651 A1 | 7/2008 | Tetzlaff et al. | |
| 2008/0217709 A1 | 9/2008 | Minervini et al. | |
| 2008/0234701 A1 | 9/2008 | Morales et al. | |
| 2008/0319442 A1 | 12/2008 | Unger et al. | |
| 2009/0012520 A1 | 1/2009 | Hixson et al. | |
| 2009/0043304 A1 | 2/2009 | Tetzlaff et al. | |
| 2009/0082766 A1 | 3/2009 | Unger et al. | |
| 2009/0082767 A1 | 3/2009 | Unger et al. | |
| 2009/0082769 A1 | 3/2009 | Unger et al. | |
| 2009/0149853 A1 | 6/2009 | Shields et al. | |
| 2009/0149854 A1 | 6/2009 | Cunningham et al. | |
| 2009/0171350 A1 | 7/2009 | Dycus et al. | |
| 2009/0171353 A1 | 7/2009 | Johnson et al. | |
| 2009/0182327 A1 | 7/2009 | Unger | |
| 2009/0248007 A1 | 10/2009 | Falkenstein et al. | |
| 2009/0248013 A1 | 10/2009 | Falkenstein et al. | |
| 2009/0248019 A1 | 10/2009 | Falkenstein et al. | |
| 2009/0248020 A1 | 10/2009 | Falkenstein et al. | |
| 2009/0248022 A1 | 10/2009 | Falkenstein et al. | |
| 2009/0292282 A9 | 11/2009 | Dycus | |
| 2009/0293288 A1* | 12/2009 | Hernandez | 30/251 |
| 2009/0306660 A1 | 12/2009 | Johnson et al. | |
| 2010/0023009 A1 | 1/2010 | Moses et al. | |
| 2010/0042100 A1 | 2/2010 | Tetzlaff et al. | |
| 2010/0100122 A1 | 4/2010 | Hinton | |
| 2010/0130971 A1 | 5/2010 | Baily | |
| 2010/0130977 A1 | 5/2010 | Garrison et al. | |
| 2010/0145334 A1 | 6/2010 | Olson et al. | |
| 2010/0179545 A1 | 7/2010 | Twomey et al. | |
| 2010/0204698 A1 | 8/2010 | Chapman et al. | |
| 2010/0280515 A1 | 11/2010 | Hixson et al. | |
| 2010/0312235 A1 | 12/2010 | Bahney | |
| 2011/0054469 A1 | 3/2011 | Kappus et al. | |
| 2011/0054472 A1 | 3/2011 | Romero | |
| 2011/0071525 A1 | 3/2011 | Dumbauld et al. | |
| 2011/0106079 A1 | 5/2011 | Garrison et al. | |
| 2011/0196368 A1 | 8/2011 | Moses et al. | |
| 2011/0218530 A1 | 9/2011 | Reschke | |
| 2011/0238067 A1 | 9/2011 | Moses et al. | |
| 2011/0257681 A1* | 10/2011 | Reschke et al. | 606/206 |
| 2012/0046659 A1 | 2/2012 | Mueller | |
| 2012/0078250 A1 | 3/2012 | Orton et al. | |

FOREIGN PATENT DOCUMENTS

| | | |
|---|---|---|
| CN | 201299462 | 9/2009 |
| DE | 2415263 | 10/1975 |
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10031773 | 11/2001 |
| DE | 19946527 | 12/2001 |
| DE | 20121161 | 4/2002 |
| DE | 10045375 | 10/2002 |
| DE | 10 2004 026179 | 12/2005 |
| DE | 20 2007 009318 | 8/2007 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 0584787 | 3/1994 |
| EP | 1159926 | 12/2001 |
| EP | 1486177 | 5/2005 |
| EP | 1532932 | 5/2005 |
| EP | 1535581 | 6/2005 |
| EP | 1609430 | 12/2005 |
| EP | 1642543 | 4/2006 |
| EP | 1645240 | 4/2006 |
| EP | 1685806 | 8/2006 |
| EP | 1769765 | 4/2007 |
| EP | 1810625 | 7/2007 |
| EP | 1929970 | 6/2008 |
| EP | 2105104 | 9/2009 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-000538 | 1/1997 |
| JP | 9-10223 | 1/1997 |
| JP | 9-122138 | 5/1997 |
| JP | 10-000195 | 1/1998 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |

(56) References Cited

FOREIGN PATENT DOCUMENTS

| | | |
|---|---|---|
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2002-136525 | 5/2002 |
| JP | 2003-116871 | 4/2003 |
| JP | 2003-175052 | 6/2003 |
| JP | 2003-245285 | 9/2003 |
| JP | 2004-517668 | 6/2004 |
| JP | 2004-528869 | 9/2004 |
| JP | 2005-152663 | 6/2005 |
| JP | 2005-253789 | 9/2005 |
| JP | 2006-015078 | 1/2006 |
| JP | 2006-501939 | 1/2006 |
| JP | 2006-095316 | 4/2006 |
| JP | 2011-125195 | 6/2011 |
| SU | 401367 | 11/1974 |
| WO | WO 94/20025 | 9/1994 |
| WO | WO 96/11635 | 4/1996 |
| WO | WO 96/22056 | 7/1996 |
| WO | WO 98/14124 | 4/1998 |
| WO | WO 00/24330 | 5/2000 |
| WO | WO 00/36986 | 6/2000 |
| WO | WO 00/47124 | 8/2000 |
| WO | WO 00/59392 | 10/2000 |
| WO | WO 01/15614 | 3/2001 |
| WO | WO 01/54604 | 8/2001 |
| WO | WO 02/07627 | 1/2002 |
| WO | WO 02/45589 | 6/2002 |
| WO | WO 02/080783 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080799 | 10/2002 |
| WO | WO 03/101311 | 12/2003 |
| WO | WO 2004/073490 | 9/2004 |
| WO | WO 2004/098383 | 11/2004 |
| WO | WO 2004/103156 | 12/2004 |
| WO | WO 2005/004734 | 1/2005 |
| WO | WO 2005/004735 | 1/2005 |
| WO | WO 2005/110264 | 11/2005 |
| WO | WO 2006/021269 | 3/2006 |
| WO | WO 2008/040483 | 4/2008 |
| WO | WO 2009/124097 | 10/2009 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 13/050,182, filed Mar. 17, 2011, Glen A. Horner.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monty S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Horner.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/360,925, filed Jan. 30, 2012, James H. Orszulak.
U.S. Appl. No. 13/400,290, filed Feb. 20, 2012, Eric R. Larson.
U.S. Appl. No. 13/404,435, filed Feb. 24, 2012, Kim V. Brandt.
U.S. Appl. No. 13/404,476, filed Feb. 24, 2012, Kim V. Brandt.
U.S. Appl. No. 13/412,879, filed Mar. 6, 2012, David M. Garrison.
U.S. Appl. No. 13/412,897, filed Mar. 6, 2012, Joanna Ackley.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/464,569, filed May 4, 2012, Duane E. Kerr.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,543, filed May 14, 2012, Sean T. Dycus.
U.S. Appl. No. 13/470,775, filed May 14, 2012, James D. Allen, IV.
U.S. Appl. No. 13/470,797, filed May 14, 2012, John J. Kappus.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/491,853, filed Jun. 8, 2012, Jessica E. Olson.
U.S. Appl. No. 13/537,517, filed Jun. 29, 2012, David N. Heard.

(56) References Cited

OTHER PUBLICATIONS

U.S. Appl. No. 13/537,577, filed Jun. 29, 2012, Tony Moua.
U.S. Appl. No. 13/550,322, filed Jul. 16, 2012, John J. Kappus.
U.S. Appl. No. 13/571,055, filed Aug. 9, 2012, Paul Guerra.
U.S. Appl. No. 13/571,821, filed Aug. 10, 2012, Joseph D. Bucciaglia.
U.S. Appl. No. 13/584,194, filed Aug. 13, 2012, Sean T. Dycus.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.

* cited by examiner

SURGICAL CLAMPING DEVICE WITH RATCHETING GRIP LOCK

BACKGROUND

1. Technical Field

The present disclosure relates to medical instruments and to the use thereof. More particularly, the present disclosure is directed to surgical clamping devices.

2. Background of Related Art

A hemostat device is a surgical instrument which relies on mechanical action between its jaws to grasp, clamp, constrict, and seal vessels or tissue. Such devices are commonly used in open, endoscopic, or laparoscopic surgical procedures. Energy-based hemostats (open or endoscopic) utilize both mechanical clamping action and energy to affect hemostasis by heating tissue and blood vessels to coagulate and/or cauterize tissue.

Certain surgical procedures require more than simply coagulating/cauterizing tissue and rely on the unique combination of clamping pressure, precise energy control, and gap distance (i.e., distance between opposing jaw members when closed about tissue) to "seal" tissue, vessels, and certain vascular bundles.

In order to effectively "seal" tissue or vessels, two predominant mechanical parameters must be accurately controlled: 1) the pressure applied to the vessel or tissue; and 2) the gap distance between the tissue contacting surfaces. As can be appreciated, both of these parameters are affected by the thickness of the tissue being sealed. Accurate application of pressure is important for several reasons: to reduce the tissue impedance to a low enough value that allows enough energy through the tissue; to overcome the forces of expansion during tissue heating; and to contribute to the end tissue thickness which is an indication of a good seal.

SUMMARY

As shown in the drawings and described throughout the following description, as is traditional when referring to relative positioning on a surgical instrument, the term "proximal" refers to the end of the apparatus that is closer to the user and the term "distal" refers to the end of the apparatus that is farther away from the user. The term "clinician" refers to any medical professional (e.g., doctor, surgeon, nurse, or the like) performing a medical procedure involving the use of embodiments described herein.

In at least one aspect of this disclosure, a surgical clamping device, comprising first and second shaft members each having a jaw member disposed at a distal end thereof, the shaft members pivotably coupled to one another and movable relative to one another between an open position and at least one closed position for moving the jaw members between a spaced-apart position and at least one approximated position, a gripping member disposed on the first shaft member, and a gear system disposed on the second shaft member and configured to receive the gripping member and incrementally lock the gripping member in at least one predefined position corresponding to the at least one approximated position of the jaw members, the gear system including a first gear rotatably connected to the second shaft member, a second gear operably connected to the first gear and movably connected to the second shaft member, and at least one locking member configured to engage one or more notches defined in the second shaft member, wherein upon movement of the first and second shaft members in a first direction, the first gear mechanically engages the gripping member thereby moving the first gear, and, in turn, the second gear such that the at least one locking member engages the notches to progressively lock the first and second shaft members from motion in a second direction.

In another aspect of this disclosure, the first and second shaft members relative movement defines a first plane, and wherein the first and second shaft members are maintained in the first plane when the gear system releases the gripping member.

In yet another aspect of this disclosure, the gripping member includes a plurality of gear teeth configured to communicate with the first gear.

In still yet another aspect of this disclosure, the surgical clamping device further comprises a release mechanism, wherein upon actuation of the release mechanism, the locking member disengages from the notches.

In still yet another aspect of this disclosure, the at least one locking member produces at least one of a tactile or audible feedback for each notch the at least one locking member engages.

In still yet another aspect of this disclosure, the one or more notches are positioned on the second shaft member to correspond to at least one predetermined clamping force produced by the jaw members in the at least one approximated position.

In still yet another aspect of this disclosure, the locking member is disposed on or forms a part of the second gear.

In still yet another aspect of this disclosure, the surgical clamping device is a hemostat.

In still yet another aspect of this disclosure, the gear system and the gripping member are made of a rigid material selected from the group consisting of one or more of a plastic, a metal, a polymer, a ceramic, an alloy, and combinations thereof.

In still yet another aspect of this disclosure, a method for clamping tissue at a predetermined force comprises providing a surgical clamping device, including first and second shaft members each having a jaw member disposed at a distal end thereof, the shaft members pivotably coupled to one another, a gripping member disposed on the first shaft member, and a gear system and one or more notches disposed on the second shaft member, the gear system including a first gear rotatably connected to the second shaft member, a second gear operably connected to the first gear and movably connected to the second shaft member, and at least one locking member, actuating the surgical clamping device to clamp tissue between the jaw members by moving the first shaft member toward the second shaft member, and engaging the gripping member and the gear system such that the locking member communicates with the one or more notches.

In still yet another aspect of this disclosure, the at least one locking member produces at least one of a tactile or audible feedback for each notch the at least one locking member engages.

In still yet another aspect of this disclosure, the method further comprises monitoring the at least one tactile or audible feedback to determine a clamping force.

In still yet another aspect of this disclosure, the method further comprises clamping tissue with a predetermined force using the surgical clamping device.

In still yet another aspect of this disclosure, the surgical clamping device is a hemostat.

In still yet another aspect of this disclosure, the gear system and the gripping member are made of a rigid material selected from the group consisting of one or more of a plastic, a metal, a polymer, a ceramic, an alloy, and combinations thereof.

In still yet another aspect of this disclosure, the locking member is disposed on or forms a part of the second gear.

In still yet another aspect of this disclosure, the notches are disposed on the second shaft member in an arcuate formation to follow a rotation of the locking member as the locking member moves with the second gear in a rotational manner.

In still yet another aspect of this disclosure, the notches are formed by an arcuate piece of material that is disposed on the second shaft member to follow a rotation of the locking member as the locking member moves with the second gear in a rotational manner.

BRIEF DESCRIPTION OF THE DRAWINGS

Various aspects of the present disclosure, by way of example only, are described herein with reference to the accompanying drawings, wherein like reference numerals refer to similar or identical elements throughout the description of the figures.

DETAILED DESCRIPTION

Figure 1:
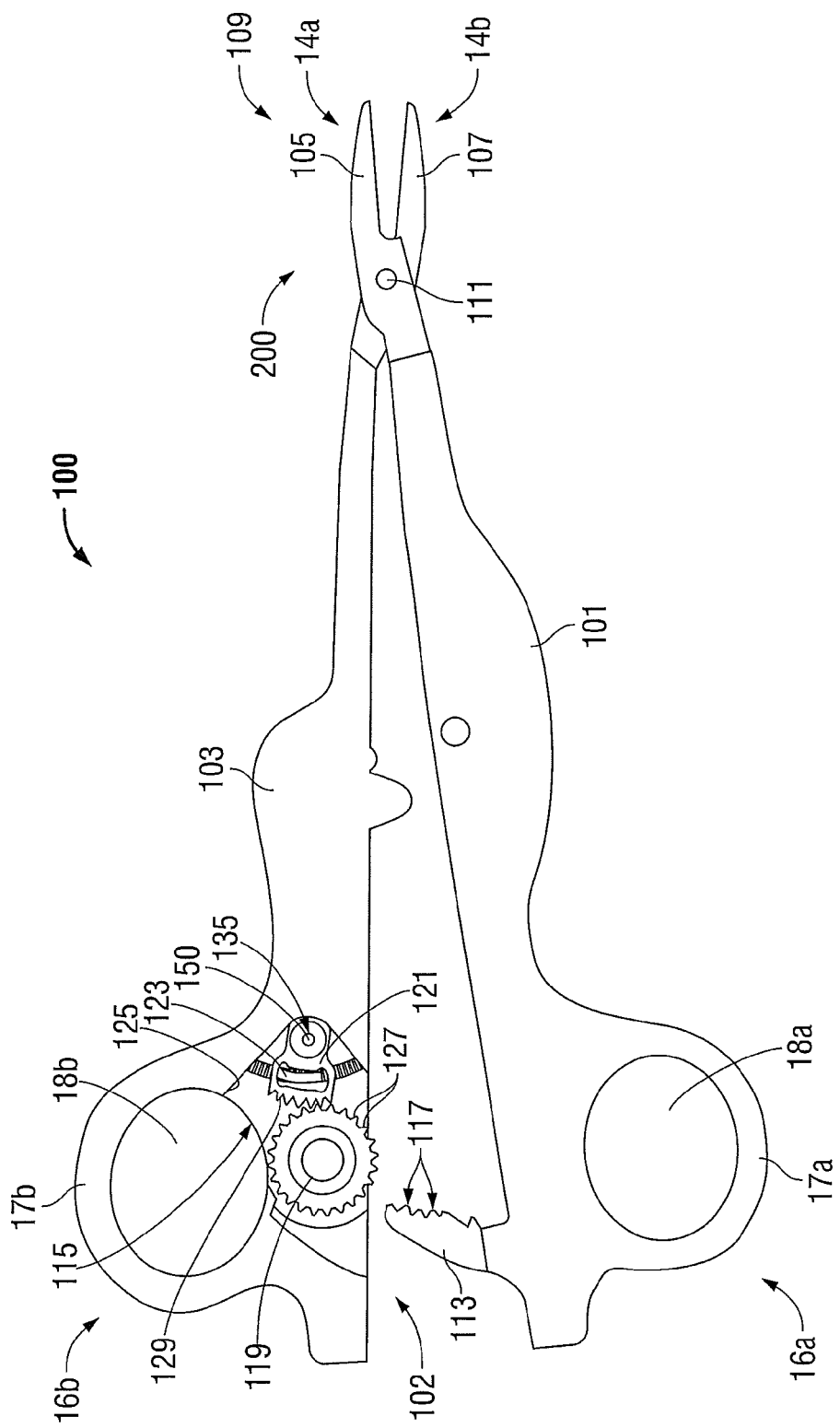
FIG. 1 illustrates an example of a surgical clamping device, in accordance with the present disclosure, in an unclamped position.

In accordance with at least one aspect of the present disclosure, a surgical clamping device 100 is disclosed. In some embodiments, a surgical clamping device is a hemostat. Referring to FIG. 1, the surgical clamping device 100 includes a first shaft member 101 and a second shaft member 103, each having a proximal end 16a and 16b, and a distal end 14a and 14b, respectively. End effector assembly 200 is attached to distal ends 14a and 14b of shafts 101 and 103, respectively. End effector assembly 200 includes a pair of opposing jaw members 105 and 107 that are pivotably connected about a pivot 111. Each shaft 101 and 103 includes a handle 17a and 17b disposed at the proximal end 16a and 16b thereof. Each handle 17a and 17b defines a finger hole 18a and 18b therethrough for receiving a finger of the user. As can be appreciated, finger holes 18a and 18b facilitate movement of the shafts 101 and 103 relative to one another which, in turn, pivots jaw members 105 and 107 from an open position, wherein the jaw members 105 and 107 are disposed in spaced-apart relation relative to one another, to one or more closed positions, wherein the jaw members 105 and 107 cooperate to grasp tissue therebetween.

A ratchet assembly 102 is included for selectively locking the jaw members 105 and 107 relative to one another at various positions during pivoting. Ratchet assembly 102 includes graduations or other visual markings that enable the user to easily and quickly ascertain and control the amount of closure force desired between the jaw members 105 and 107. Alternatively or additionally, audible and/or tactile feedback may be provided to provide feedback to the user relating the degree of engagement of various components of the ratchet assembly 102 as described in greater detail hereinbelow.

One or both of the shafts 101, 103 are configured to connect the clamping device 100 to a source of energy such as a generator (not shown) such that the clinician may selectively apply energy to the jaw members 105 and 107 for treating tissue grasped therebetween. Clamping device 100 may further include a knife assembly (not shown) disposed within either of shafts 101, 103 and a knife channel (not shown) defined within one or both jaw members 105 and 107 to permit reciprocation of a knife blade (not shown) therethrough to divided previously-treated tissue (or to simply cut tissue, where tissue-treatment is not desired).

Figure 2:
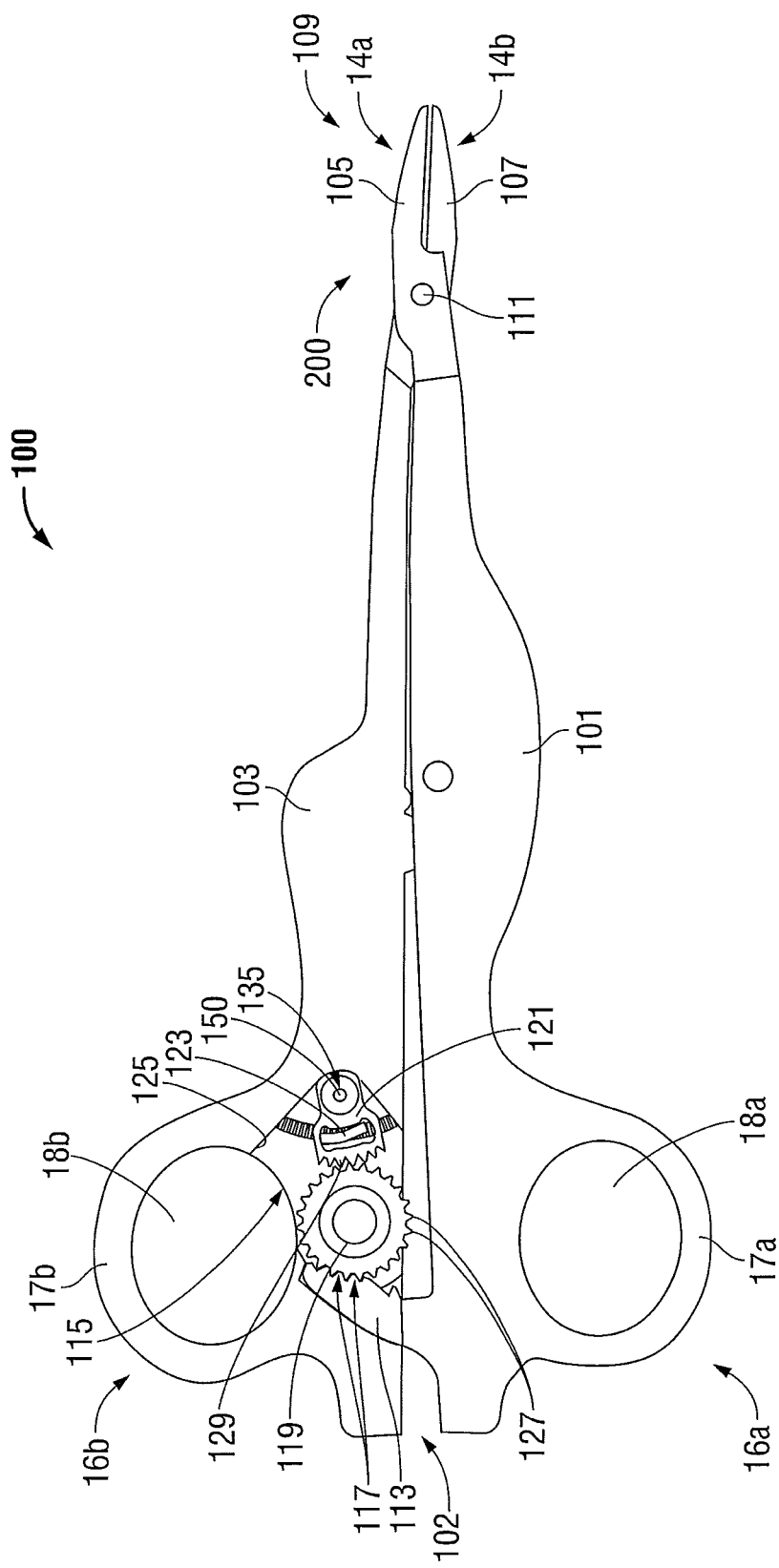
FIG. 2 illustrates the surgical clamping device of FIG. 1 in a clamped position.
Figure 3:
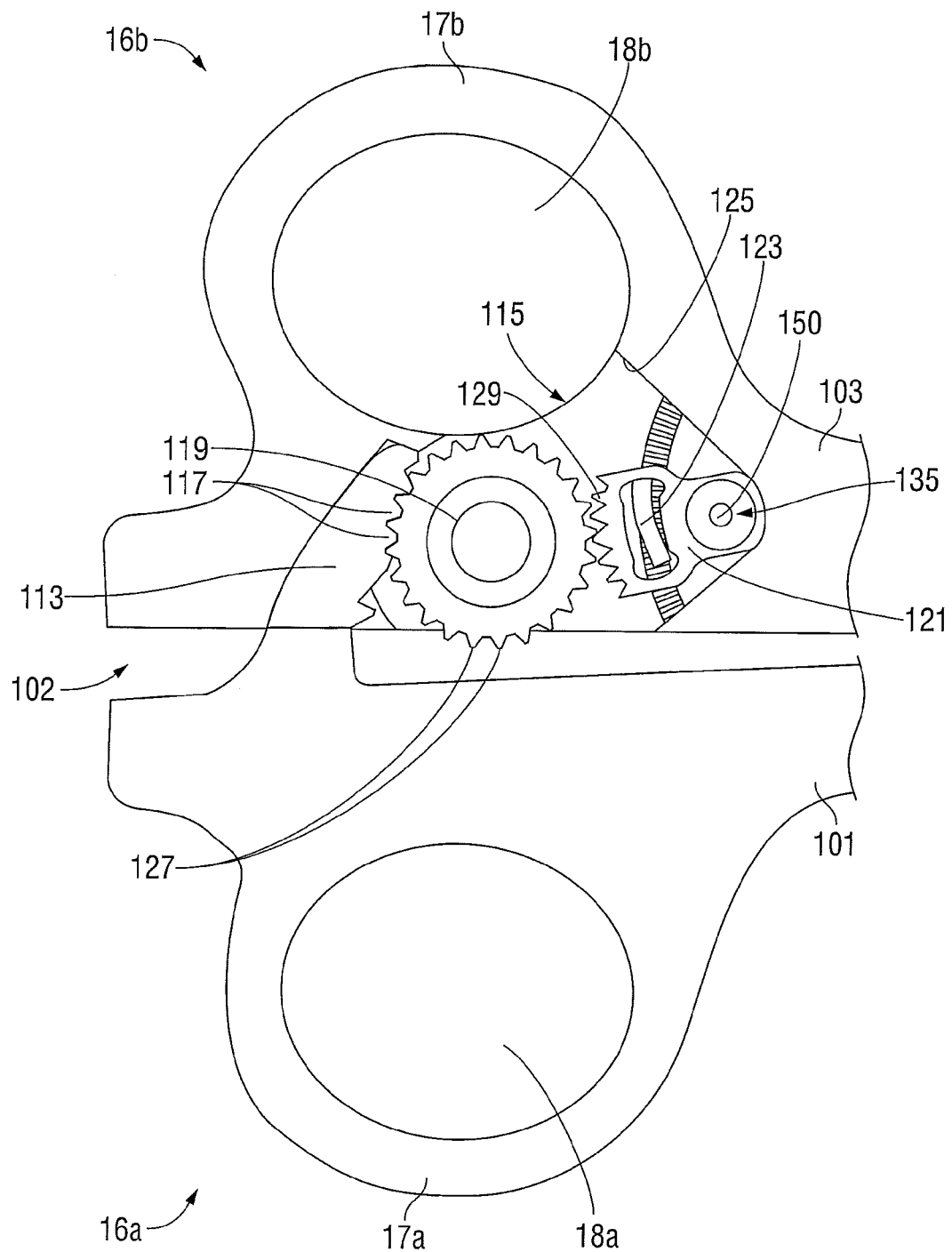
FIG. 3 illustrates an enlarged view of the area of detail of FIG. 1 showing a ratchet assembly of the surgical clamping device.

The shaft members 101, 103 are movable relative to one another between an open position (as shown in FIG. 1), and at least one closed position (as shown in FIGS. 2 and 3) for moving the jaw members 105, 107 between a spaced-apart position (as shown in FIG. 1) and at least one approximated position (as shown in FIGS. 2 and 3). The first and second shaft members 101, 103 may be movable in substantially parallel planes.

Ratchet assembly 102 includes a gripping member 113 that is disposed on the first shaft member 101 and includes one or more protrusions 117 extending therefrom. The protrusions 117 may be gear teeth configured to communicate with one or more corresponding gears as described herein.

The ratchet assembly 102 further includes a gear system 115 disposed on the second shaft member 103 and configured to mechanically engage the gripping member 113. The gear system 115 incrementally locks the gripping member 113 (and thus first shaft 101) in a predefined position relative to the second shaft member 103 as the shaft members 101 and 103 are approximated relative to one another. In some embodiments, the shaft members 101, 103 relative movement defines a first plane and the gear system 115 releases the gripping member 113 without moving either the shaft members 101, 103 outside of the first plane, e.g. without requiring movement of the shaft member 101, 103 laterally towards or away from one another.

Gear system 115 includes a first gear or cog 119 rotatably connected to the second shaft member 103. The first gear 119 includes gear teeth 127 that are configured to engage and/or pair with the gear teeth 117 of gripping member 113. The gear ratio and tooth size of gear 119 may be selected as desired for the intended use. Gear system 115 further includes a second gear 121 operably connected to the first gear 119 and movably connected to the second shaft member 103. The second gear 121 includes gear teeth 129 that interact and/or pair with the gear teeth 127 of first gear 119.

The gear system and the gripping member may be made of a rigid material including, but not limited to, one or more of a plastic, a metal, a polymer, a ceramic, an alloy, and combinations thereof.

Gear system 115 further includes a spring (e.g., a rotational spring) (not shown) connected to the second gear 121 which biases the second gear 121 against the first gear 119 as the gripping member 113 advances the first gear 119 during approximation.

At least one locking member 123 is configured to grip one or more notches 125 disposed on the second shaft member 103. In some embodiments, the locking member 123 is disposed on or forms a part of the second gear 121.

More particularly, the locking member 123 engages the one or more notches 125 in a progressive manner such that when the lock member 123 is moved over a notch 125, a portion of locking member 123 engages the notch 125 and prevents the locking member 123 from returning to a previous position. In this instance, the locking member 123 may be configured to produce a tactile or audible click as the locking member 123 progresses over successive notches 125.

The locking member 123 is selectively released from the notch 125 via a release mechanism 135 such as, but not limited to, a button or lever (not shown) disposed on the second shaft portion 103 or second gear 121. Upon actuation of the release mechanism 135, the locking member 123 disengages from a given notch 125. For example, release mechanism 135 may push or pull the second gear 121 and/or locking member 123 to dislodge the locking member 123 from the notch 125 by slideably moving the second gear 121 on hinge 150 (hinge 150 may be slideable relative to the second shaft portion 103 such that the second gear 121 or locking member 123 move with the hinge 150 as it is pushed or pulled). A spring (not shown) may bias the second gear member 121 or locking member 123 in locking position with the repective notch(s) 125. In this instance, the gear system 115 can selectively release the gripping member 113 without moving either the first or second shaft members 101, 103 relative to one another, thus maintaining the plane formed by shaft members 101, 103.

The one or more notches 125 are configured to allow the locking member 123 to move across the one or more notches 125 while progressively snapping into each successive notch 125 when the locking member 123 is advanced in a first direction, for example, in the direction of the first shaft portion 101. The one or more notches 125 prevent the locking member 123 from moving in a second direction preventing the ratcheting system 115 from reverse motion while the locking member 123 is engaged with a particular notch 125.

The one or more notches 125 may be integral, overlaid, carved, or inlayed on the second shaft member 103. Alternatively, the one or more notches 125 may be a separate piece of material attached to the second shaft member 103 in any suitable manner.

The one or more notches 125 may be any shape as desired to facilitate engagement and release from the locking member 123. For example, the one or more notches may be disposed along an arcuate piece of material as shown in FIGS. 1-3.

Moreover, the one or more notches 125 may be positioned on the second shaft member 103 to correspond to one or more predetermined clamping forces produced by the jaw members 105, 107 when approximated. For example, one or more positions may correspond to closure pressures at the jaw members 105, 107 to between about 3 kg/cm^2 to 16 kg/cm^2, which are closure pressures particularly suited for vessel sealing, although other closure pressures may be provided.

In use, a clinician may move the first shaft member 101 and the second shaft member 103 together to close the jaw members 105, 107 from the open position as shown in FIG. 1, to the closed position, as shown in FIGS. 2 and 3. As the first shaft member 101 advances toward the second shaft member 103, the gripping member 113 advances toward the first gear 119.

Referring to FIGS. 2 and 3, the first gear 119 is configured to engage the gripping member 113 and be advanced thereby. For example, as the gripping member 113 is advanced further in the direction of the second shaft portion 103, the gripping member 113 engages first gear 119 and first gear 119 rotates in a first direction with further advancement of the gripping member 113. As the first gear 119 rotates, the second gear 121 rotates in a second direction. The second gear 121, being operably connected to the locking member 123, moves the locking member 123 across or over successive notches 125. As mentioned above, the locking member 123 produces a tactile or audible feedback (click) as it passes each notch 125. The ratio of gear teeth determines the frequency of the feedback (clicks).

By listening or sensing the feedback (clicks), a clinician can determine and/or select the amount of clamping force being applied at the jaw members 105, 107 by the clamping device 100. Once the desired force setting is reached, the clinician simply stops advancing the first shaft member 101 toward the second shaft member 103 and, at this point, the locking member 123 is engaged with a corresponding notch 125 to lock the gear system 115. In this position, the first shaft member 101 can not pull away from the second shaft member 103 (i.e., reverse rotation of gear 119) as long as the gripping member 113 engages the first gear 119.

The restoring force of a mass e.g., tissue, being clamped in the jaw members 105, 107, or the material restoring force of the two jaw members 105, 107 being forced together will produce an opposing force tending to pull the first shaft member 101 away from the second shaft member 103. However, as disclosed above, when in the locked state, the gear system 115 does not allow the release of the gripping member 113 and, thus, the first shaft member 101 cannot be forced away from the second shaft member 103 due to the restoring force. Thus, a desired clamping pressure about tissue can be maintained.

To release the locking member 123 from the corresponding notch 125, the clinician activates the release mechanism 135 to dislodge the locking member 123 from the notch 125. When the locking member 123 is disengaged, the gear system 115 is free to operate in reverse motion (i.e., allow gripping member 113 to pull the first gear 119 in the reverse direction) thereby allowing the first shaft member 101 to move in the direction away from the second shaft member 103 and unclamp jaw members 105, 107. The clinician does not need to move the first shaft member 101 and the second shaft member 103 laterally (out of the plane defined therebetween) to release the gear system as with conventional systems.

In another embodiment of the present disclosure, a method for clamping tissue with a predetermined force is further disclosed. The method includes providing a surgical clamping device 100 as described above, actuating the surgical clamping device 100 to clamp tissue by moving the first shaft member 101 toward the second shaft member 103; and engaging the gripping member 113 and the gear system 115 such that the locking member 123 engages a corresponding notch 125. The method may further include monitoring the tactile or audible feedback to determine a clamping force.

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

What is claimed is:

1. A surgical clamping device, comprising:
   first and second shaft members each having a jaw member disposed at a distal end thereof, the shaft members pivotably coupled to one another and movable relative to one another between an open position and at least one closed position for moving the jaw members between a spaced-apart position and at least one approximated position;
   a gripping member disposed on the first shaft member; and
   a gear system disposed on the second shaft member and configured to receive the gripping member and incrementally lock the gripping member in at least one predefined position corresponding to the at least one approximated position of the jaw members, the gear system including:
   a first gear rotatably connected to the second shaft member;
   a second gear operably connected to the first gear and movably connected to the second shaft member; and at least one locking member configured to engage one or more notches defined in the second shaft member, wherein upon movement of the first and second shaft members in a first direction, the first gear mechanically engages the gripping member thereby moving the first gear, and, in turn, the second gear such that the at least one locking member engages the notches to progressively lock the first and second shaft members from motion in a second direction.

2. The surgical clamping device of claim 1, wherein the first and second shaft members relative movement defines a first plane, and wherein the first and second shaft members are maintained in the first plane when the gear system releases the gripping member.

3. The surgical clamping device of claim 1, wherein the gripping member includes a plurality of gear teeth configured to communicate with the first gear.

4. The surgical clamping device of claim 1, further comprising a release mechanism, wherein upon actuation of the release mechanism, the locking member disengages from the notches.

5. The surgical clamping device of claim 1, wherein the at least one locking member produces at least one of a tactile or audible feedback for each notch the at least one locking member engages.

6. The surgical clamping device of claim 1, wherein the one or more notches are positioned on the second shaft member to correspond to at least one predetermined clamping force produced by the jaw members in the at least one approximated position.

7. The surgical clamping device of claim 1, wherein the locking member is disposed on or forms a part of the second gear.

8. The surgical clamping device of claim 1, wherein the surgical clamping device is a hemostat.

9. The surgical clamping device of claim 1, wherein the gear system and the gripping member are made of a rigid material selected from the group consisting of one or more of a plastic, a metal, a polymer, a ceramic, an alloy, and combinations thereof.

10. A method for clamping tissue at a predetermined force, comprising:
   providing a surgical clamping device, including:
      first and second shaft members each having a jaw member disposed at a distal end thereof, the shaft members pivotably coupled to one another;
      a gripping member disposed on the first shaft member; and
      a gear system and one or more notches disposed on the second shaft member, the gear system including:
         a first gear rotatably connected to the second shaft member;
         a second gear operably connected to the first gear and movably connected to the second shaft member; and
         at least one locking member;
   actuating the surgical clamping device to clamp tissue between the jaw members by moving the first shaft member toward the second shaft member; and
   engaging the gripping member and the gear system such that the locking member communicates with the one or more notches.

11. The method of claim 10, wherein the at least one locking member produces at least one of a tactile or audible feedback for each notch the at least one locking member engages.

12. The method of claim 11, further comprising monitoring the at least one tactile or audible feedback to determine a clamping force.

13. The method of claim 12, further comprising clamping tissue with a predetermined force using the surgical clamping device.

14. The method of claim 10, wherein the surgical clamping device is a hemostat.

15. The method of claim of claim 10, wherein the gear system and the gripping member are made of a rigid material selected from the group consisting of one or more of a plastic, a metal, a polymer, a ceramic, an alloy, and combinations thereof.

16. The method of claim of claim 10, wherein the locking member is disposed on or forms a part of the second gear.

17. The method of claim 16, wherein the notches are disposed on the second shaft member in an arcuate formation to follow a rotation of the locking member as the locking member moves with the second gear in a rotational manner.

18. The method of claim 16, wherein the notches are formed by an arcuate piece of material that is disposed on the second shaft member to follow a rotation of the locking member as the locking member moves with the second gear in a rotational manner.

* * * * *